United States Patent [19]

Jay

[11] Patent Number: 5,497,426
[45] Date of Patent: Mar. 5, 1996

[54] STETHOSCOPIC SYSTEM FOR HIGH-NOISE ENVIRONMENTS

[76] Inventor: Gregory D. Jay, 3 Crossbow Rd., Norfolk, Mass. 02056

[21] Appl. No.: 153,413

[22] Filed: Nov. 15, 1993

[51] Int. Cl.$^6$ ........................................... A61B 7/04
[52] U.S. Cl. ....................................... 381/67; 381/71
[58] Field of Search ................................ 381/71, 72, 67

[56] References Cited

U.S. PATENT DOCUMENTS

| | | |
|---|---|---|
| 3,385,930 | 5/1968 | Harshbarger ............................ 381/67 |
| 4,220,160 | 9/1980 | Kimball et al. . |
| 4,455,675 | 6/1984 | Bose et al. . |
| 4,494,074 | 1/1985 | Bose . |
| 4,528,690 | 7/1985 | Sedgwick . |
| 4,644,581 | 2/1987 | Sapiejewski . |
| 4,783,814 | 11/1988 | Foley . |
| 4,783,818 | 11/1988 | Graupe et al. . |
| 4,784,154 | 11/1988 | Shirley et al. . |
| 4,837,832 | 6/1989 | Fanshel . |
| 4,941,187 | 7/1990 | Slater .................................. 381/86 |
| 4,985,925 | 1/1991 | Langberg et al. . |
| 5,117,461 | 5/1992 | Moseley . |
| 5,131,047 | 7/1992 | Hashimoto et al. . |
| 5,134,659 | 7/1992 | Moseley . |
| 5,138,663 | 8/1992 | Moseley . |
| 5,138,664 | 8/1992 | Kimura et al. . |
| 5,182,774 | 1/1993 | Bourk ................................... 381/72 |
| 5,251,263 | 10/1993 | Andrea et al. ....................... 381/71 |

OTHER PUBLICATIONS

An Experimental Electronic Stethoscope for Aircraft Use Authors: Brogan, Collins, Wing; Aug. 1966.

*Primary Examiner*—Forester W. Isen
*Attorney, Agent, or Firm*—Charles W. Hanor; Kirt S. O'Neill

[57] ABSTRACT

An electronic stethoscopic system is described which permits detection of auscultory sounds in a patient in high noise environments such as ambulances and aircraft. The stethoscope employs an electroacoustical transducer, an acoustical driver mounted in a headset providing acoustical isolation from exterior noise, a summing microphone positioned within the insulating headset, and active noise reduction circuitry to feed an error signal back from the summing microphone to the acoustical driver so as to effectively cancel the unwanted acoustical noise originating external to the insulating headset. The stethoscopic system includes circuitry permitting the headset to selectively receive the audio output from a vehicular intercom system whenever a voice signal is present, thereby allowing treating medical personnel to monitor the patient while participating in the conversation being conducted on the vehicle's intercom system.

3 Claims, 5 Drawing Sheets

STETHOSCOPIC SYSTEM FOR HIGH-NOISE ENVIRONMENTS

BACKGROUND OF THE INVENTION

The invention relates generally to electronic stethoscopes, and more particularly to electronic stethoscopes employing active noise reduction circuitry to permit detection of auscultory sounds in patients in high ambient noise environments such as aircraft or moving ambulances.

The Gosport tube is presently the most common type of stethoscope, employing a diaphragm for conduction of sound through rubber tubing into binaural earplugs. Electronic stethoscopes are available which use in-line electronic amplifiers to boost low-frequency auscultory sounds that typically lie in the frequency range between 10 Hz and 250 Hz. Regardless of amplification, the Gosport tube approach to auscultation fails in areas of high ambient noise. Trauma rooms, ambulances, and aircraft are examples of areas plagued by low frequency background sounds. In the case of helicopter operations these sounds may reach amplitudes of 120 dB. Regardless of the degree of amplification of heart and lung sounds, the signal-to-noise ratio remains high and usually preclude useful listening.

Current ambient noise reduction techniques have proved to be of only marginal value to stethoscopic applications for aircraft and the like. It is known that ambient noise penetrating the transducer wall can be reduced by low-pass filtering the transducer output, or by the use of heavy acoustical shielding around the body of the transducer to enhance the ausculation sounds emanating from the body wall of the patient. An electronic stethoscope employing low-pass filtering combined with passive shielding of the pickup transducer is disclosed in Brogan, F. A., Collins, F. G., and Wing, M. E., *An Experimental Electronic Stethoscope for Aircraft Use*, USAF Rep. No. SAM-TR-67-39 (1966). These techniques, however, are ineffective to reduce ambient noise impinging directly on the ear.

One approach to reducing ambient noise at the ear of the listener is to employ a negative feedback loop from a summing microphone located near the ear canal to the speaker generating the desired audio signal, in effect broadcasting "anti-noise" to cancel the ambient noise. It is known to use negative feedback of a noisy audio signal to reduce ambient noise ("active noise reduction") in a stethoscopic application. U.S. Pat. No. 4,985,925 issued to Langberg et al. discloses active noise reduction circuitry for a stethoscope having earplugs. Such a stethoscope, however, still has the disadvantage that, in extremely high ambient noise environments, the ambient noise impinging on the summing microphone is of such a magnitude that the speaker cannot generate a sufficiently strong "anti-noise" signal to cancel the noise signal.

Moreover, a stethoscope user in evacuation and transportation vehicles often needs to be in communication with others in the vehicle but has difficulty alternating between his stethoscope and the vehicle's intercom system. This situation commonly occurs in combat aircraft, where the medical personnel may also be part of the flight crew. A disadvantage of the prior art stethoscopes is that they are not integrable into the intercom system of an evacuation or transportation vehicle.

Accordingly, an object of the present invention is to provide an improved stethoscopic system for reducing high ambient noise in environments such as aircraft, ambulances, and the like.

Another object of the present invention is to provide a stethoscopic system that is easily integrable into a vehicular intercom system to permit medical personnel to contemporaneously monitor the patient and communicate with other personnel in the vehicle.

Other objects of the present invention will become apparent from the specification.

SUMMARY OF THE INVENTION

In the invention, a conventional acoustoelectrical transducer converts auscultory sounds into an electrical signal. An amplifier provides high-gain amplification in the frequency range of the auscultory sounds. The amplified signal is fed to an acoustical driver mounted in a headset.

Also mounted in the headset, at a point as near as practicable to the listener's ear, is a microphone whose input is the sum of the desired auscultory sounds and unwanted acoustical noise that originates from outside the headset. Large passive ambient noise reduction at the ear of the listener is achieved by the use of a close-fitting headset of the type typically used in aviation applications. The headset forms an acoustical seal to passively reduce ambient noise impinging on the listener's ear.

After being passively attenuated by the headset, this unwanted acoustical noise is further reduced by active means. Feedback circuitry introduces a phase-shifted version of the output of the summing microphone into the acoustical driver, and the resultant acoustical signal tends to cancel the ambient noise near the ear.

The input terminal of the headset is connected to the output of the amplifier by a switch. During normal operation, the switch is closed for auscultation. The switch is controlled by a voice-activated circuit which detects the presence of a voice signal at the output terminal of a vehicular intercom system. When a voice signal is present, the switch is opened to connect the input terminal of the headset to the output terminal of the intercom system; otherwise, the switch remains closed.

DESCRIPTION OF THE PREFERRED EMBODIMENTS

Figure 1:
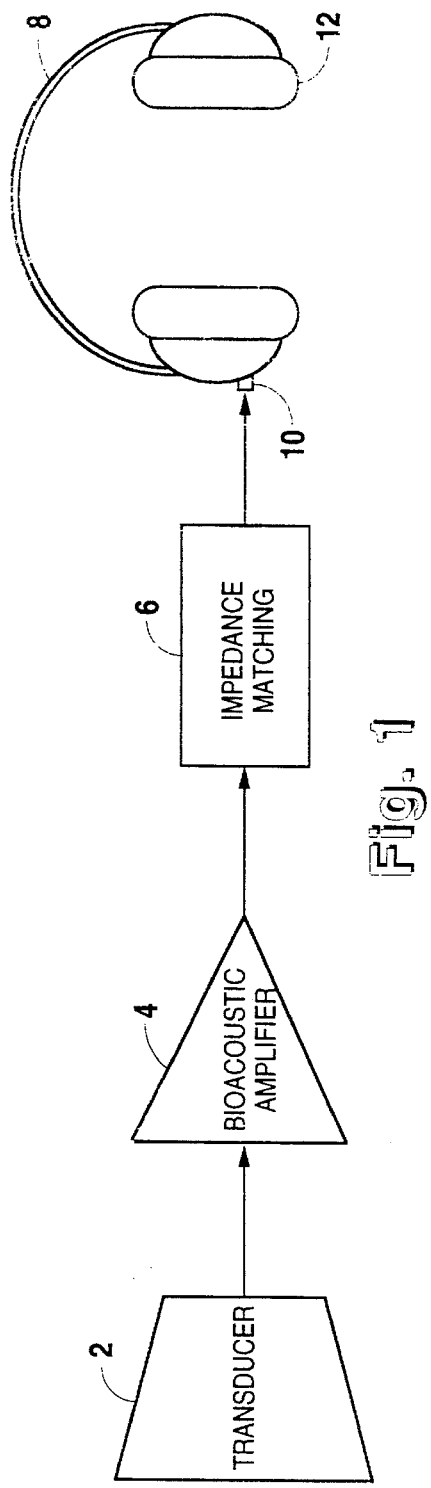
FIG. 1 is a block diagram of an electronic stethoscope for use in high-noise environments, with active noise reduction circuitry and a passive-noise-reducing headset.

FIG. 1 shows a block diagram of an electronic stethoscope for high-noise environments. The transducer 2 converts auscultory sounds into an electronic signal that feeds the bioacoustic amplifier 4. Impedance matching circuitry 6 matches the output impedance of the bioacoustic amplifier to the input impedance of the headset 8 employing active noise reduction technology. The headset has an input jack 10 and acoustical shielding 12 to present a passive acoustical barrier to external noise.

The transducer 2 is a dynamic microphone with an augmented low-frequency response. In the preferred embodiment, the microphone is a model VS40S, available from Project Unlimited. Alternatively, the transducer may be an electret microphone element housed in a standard stethoscope bell turnable to either a diaphragm or open face. In either case, a substantially flat seal is formed against the skin, affording a modicum of attenuation of external low-frequency noise. The bioacoustic amplifier 4 is designed to provide maximum amplification in the frequency range occupied by auscultory sounds, typically 10 Hz to 250 Hz, and the particulars of its design are discussed below in connection with the description of FIG. 4.

The headset 8 employs both active noise reduction technology and heavy passive shielding of exterior noise. In the preferred embodiment, the BOSE Aviation Headset is connected to the bioacoustic amplifier at input jack 10. Impedance matching circuitry 6 is a 6:1 transformer, which matches the 8 ohm output impedance of the bioacoustic amplifier to the 300 ohm input impedance of the headset.

Figure 2:
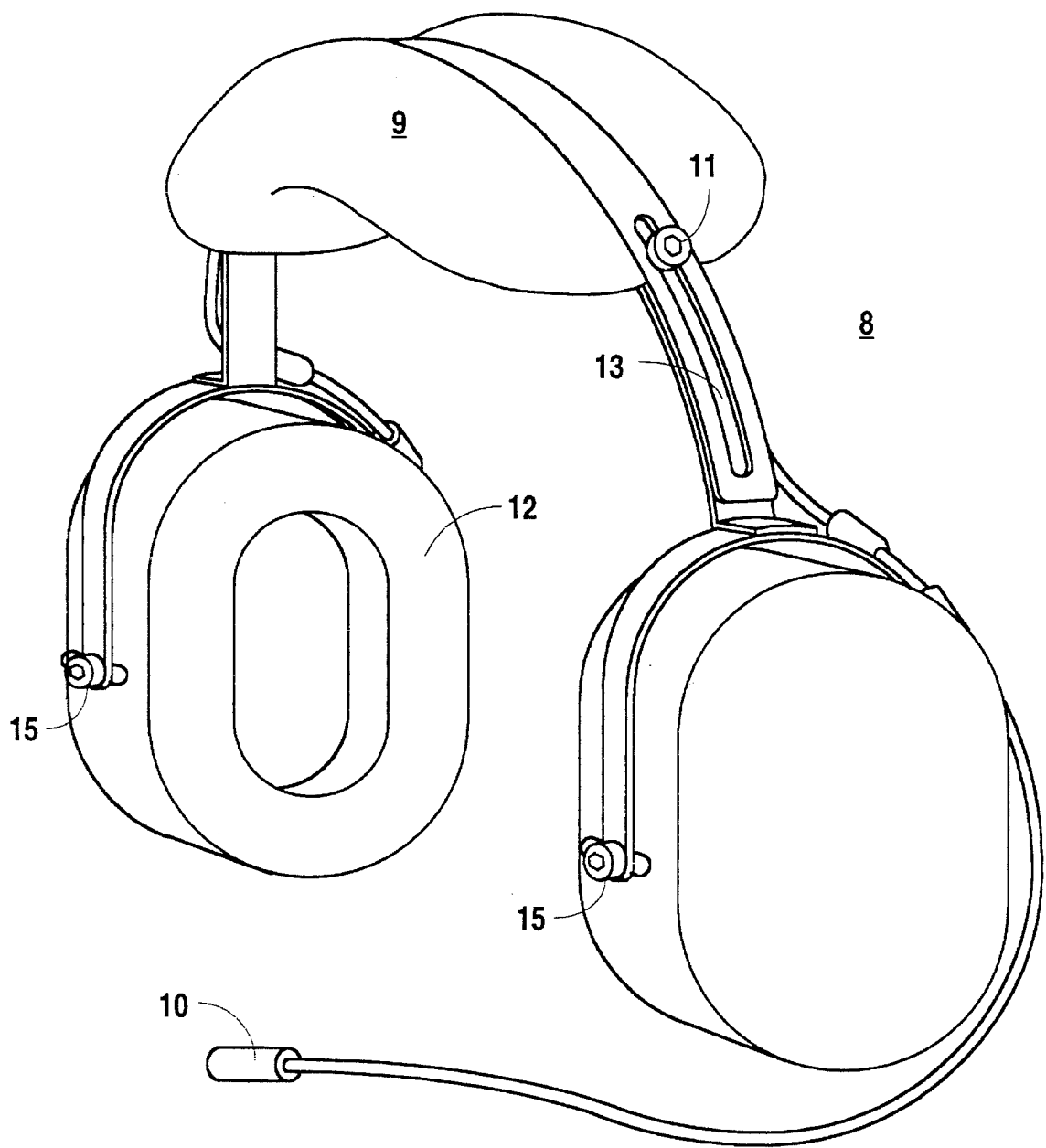
FIG. 2 is a perspective view of a passive-noise-reducing headset employing a close-fitting acoustical shield to passively attenuate ambient noise.

FIG. 2 shows a perspective view of the passive-noise-reduction headset which houses the active-noise-reduction circuitry. The close-fitting acoustical shielding 12 conforms to individual head contours. The shielding is preferably a casing formed of soft, pliable material and filled with a combination of silicon gel and soft foam to cushion the headset from the head of the user. The headset may be provided with a crown cushion 9 for added comfort. Each earpiece of the headset is provided with a capped pin 11 which is retained in slot 13 and slides in the slot for downward or upward adjustment of each earpiece. Additional adjustment of the position of each earpiece of the headset is obtained by rotating each earpiece on hinge 15. Adjustment of the headset on the user's head by manipulation of hinges 15 and the combination of capped pins 11 and slots 13 permits the user to obtain the closest fit of acoustical shielding 12, and hence the greatest amount of passive reduction of ambient noise.

Figure 3:
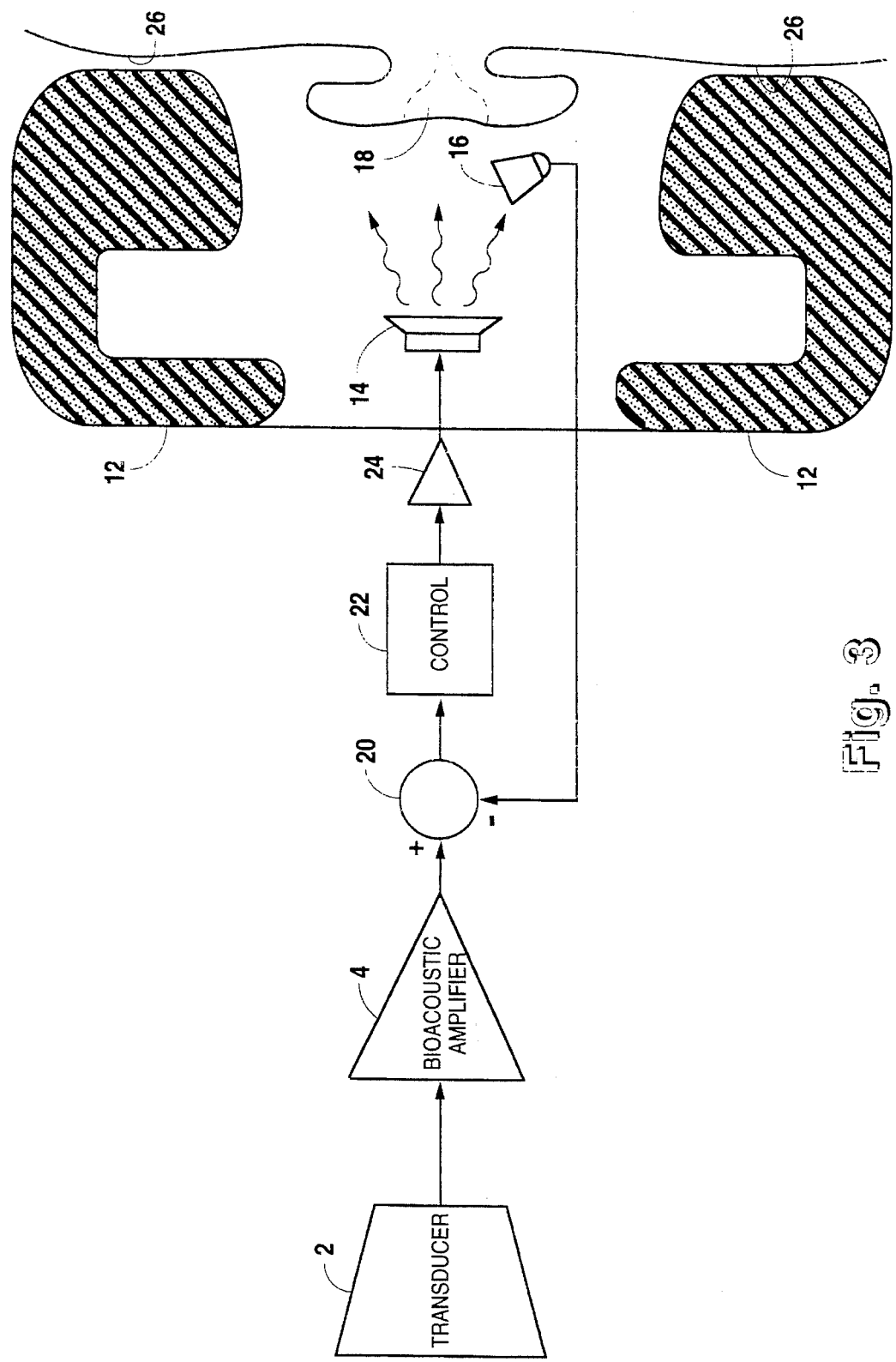
FIG. 3 is a cross-sectional view of a passive-noise-reducing headset showing the driver and summing microphone used for active noise reduction positioned in the headset.

FIG. 3 shows a cross-sectional view of a passive-noise-reducing headset showing the driver and summing microphone used for active noise reduction positioned in the headset. As noted, the headset is the BOSE Aviation Headset. In the headset, the output of the bioacoustic amplifier 4 is fed to the electroacoustical driver 14, which emits the desired acoustical pressure wave toward the ear. A summing microphone 16 is mounted in the headset near the ear canal 18 to pick up both the desired sound and noise originating external to the headset. The output of the summing microphone is fed back and subtracted at the signal combiner 20. Control circuitry 22 filters the output of the signal combiner and controls the gain of amplifier 24, which drives the driver 14 to produce an acoustical pressure signal tending to cancel external noise at a point near the ear canal 18. In the BOSE headset, the active noise reduction circuitry comprising the signal combiner 20, the control circuitry 22, and the amplifier 24, is mounted in the headset, although it is understood that they need not be an integral part of the headset.

The headset has a heavy acoustical shield 12 that forms a close-fitting seal with the head surface 26 of the listener. The acoustical shield is specially designed to shield against the particular frequencies anticipated to occur in the ambient noise. In the preferred embodiment, the acoustical shield is a combination of silicon gel and soft foam, which enables the headset to conform to the head surface 26 with minimum pressure exerted thereon.

Figure 4:
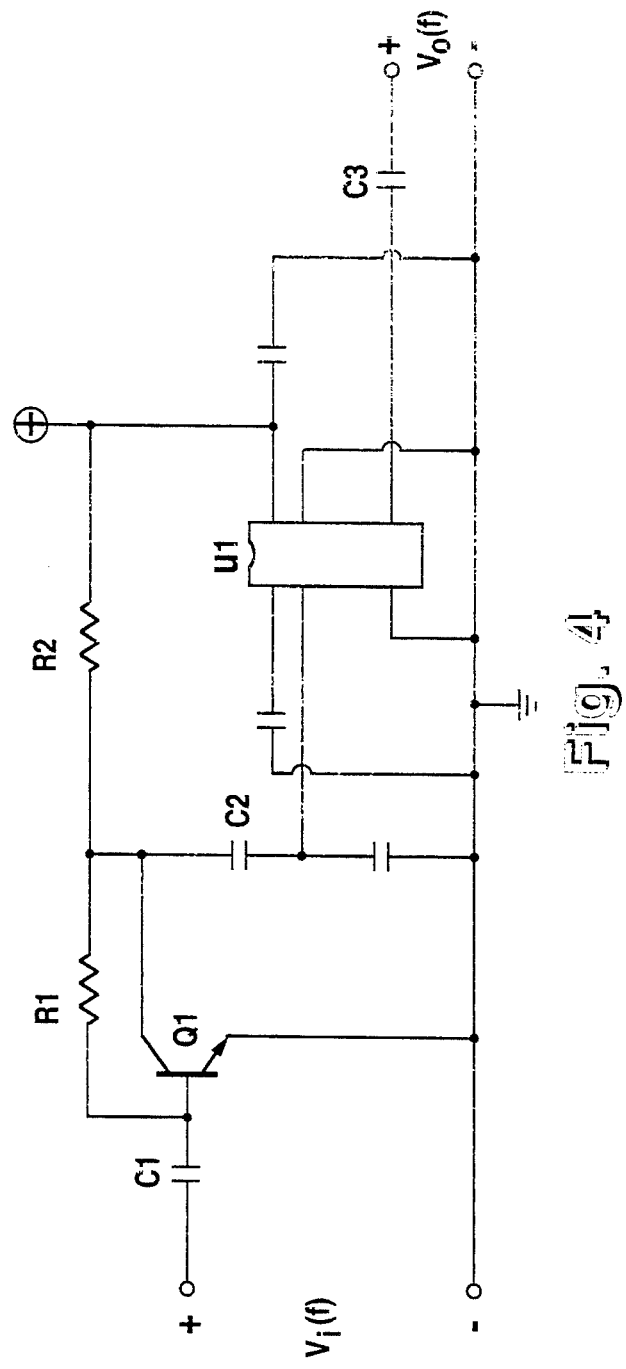
FIG. 4 is a circuit schematic of an in-line amplifier for the electronic stethoscope.

FIG. 4 shows the circuit schematic of a bioacoustic amplifier. The amplifier of the preferred embodiment is a two-stage amplifier having an overall gain of approximately 3000. In the first stage, the input from the transducer, $V_i(f)$, is connected through coupling capacitor C1 to an audio preamplifier formed by n-p-n transistor Q 1. The gain of the audio preamplifier is proportional to the ratio of resistor R1 to resistor R2, and is approximately 60 in the preferred embodiment. The output of Q1 is connected through coupling capacitor C2 to the input of second-stage amplifier U1, which is preferably the LM380, available from Texas Instruments. U1 has a nominal gain of 50 and an audio power output of approximately 2.5 Watts. The output of U1, $V_o(f)$, is fed to impedance matching circuitry via coupling capacitor C3.

Figure 5:
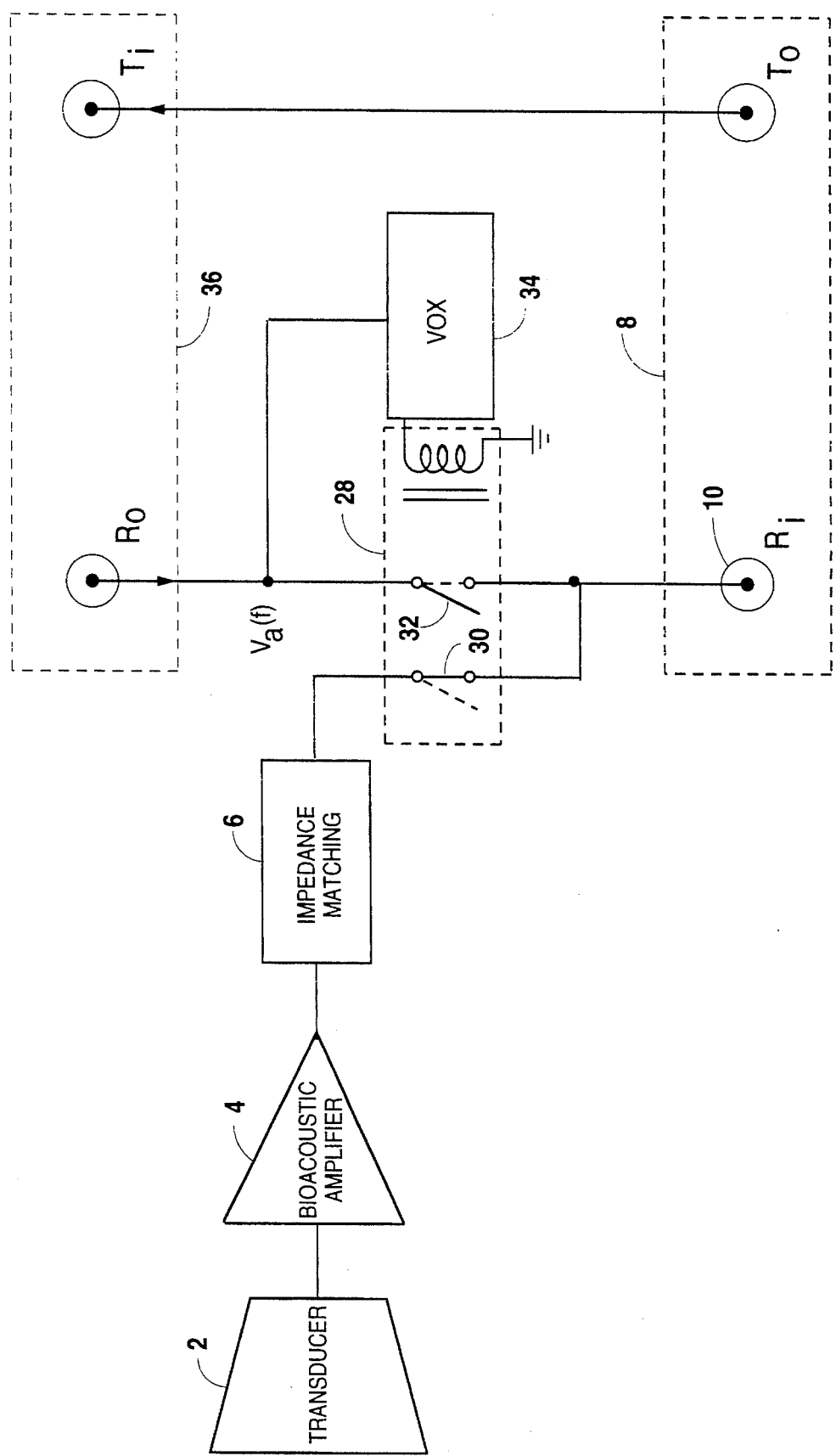
FIG. 5 is a block diagram of an electronic stethoscope integrable into a vehicular intercom system.

In accordance with the invention, FIG. 5 is a block diagram of an electronic stethoscope integrable into a vehicular intercom system. The output of impedance matching circuitry 6 is connected to the input jack 10 of headset 8 through switch arm 30 of relay switch 28. Relay switch 28 is a DPDT switch configured so that switch arm 30 is open when switch arm 32 is closed, and switch arm 30 is closed when switch arm 32 is open. In the quiescent state, switch arm 30 is closed, and the stethoscope supplies the audio signal received in the headset 8 at terminal $R_i$. When crew communications is present on the vehicular intercom, the voice-activated circuit (VOX) 34 senses the audio signal $V_a(f)$ present at terminal $R_o$, the output terminal of the vehicular intercom system 36. In response to the audio signal, VOX 34 causes switch arm 30 of relay switch 28 to open, and correspondingly closing switch arm 32 so that crew communications from the vehicular intercom system supplies the audio to the headset at terminal $R_i$. In the preferred embodiment, the headset is also equipped with voice output terminal $T_o$ to enable the wearer to communicate with the crew by transmitting audio to the input terminal $T_i$ of the vehicular intercom system.

Alternatively, VOX 34 and relay switch 28 could be replaced with a manually operated switch. Such a configuration would permit the headset wearer to determine whether he hears auscultory sounds or crew communications. Also, a manual switch could be used in conjunction with VOX 34 to provide a manual override function, although this is not the preferred embodiment.

Figure 6:
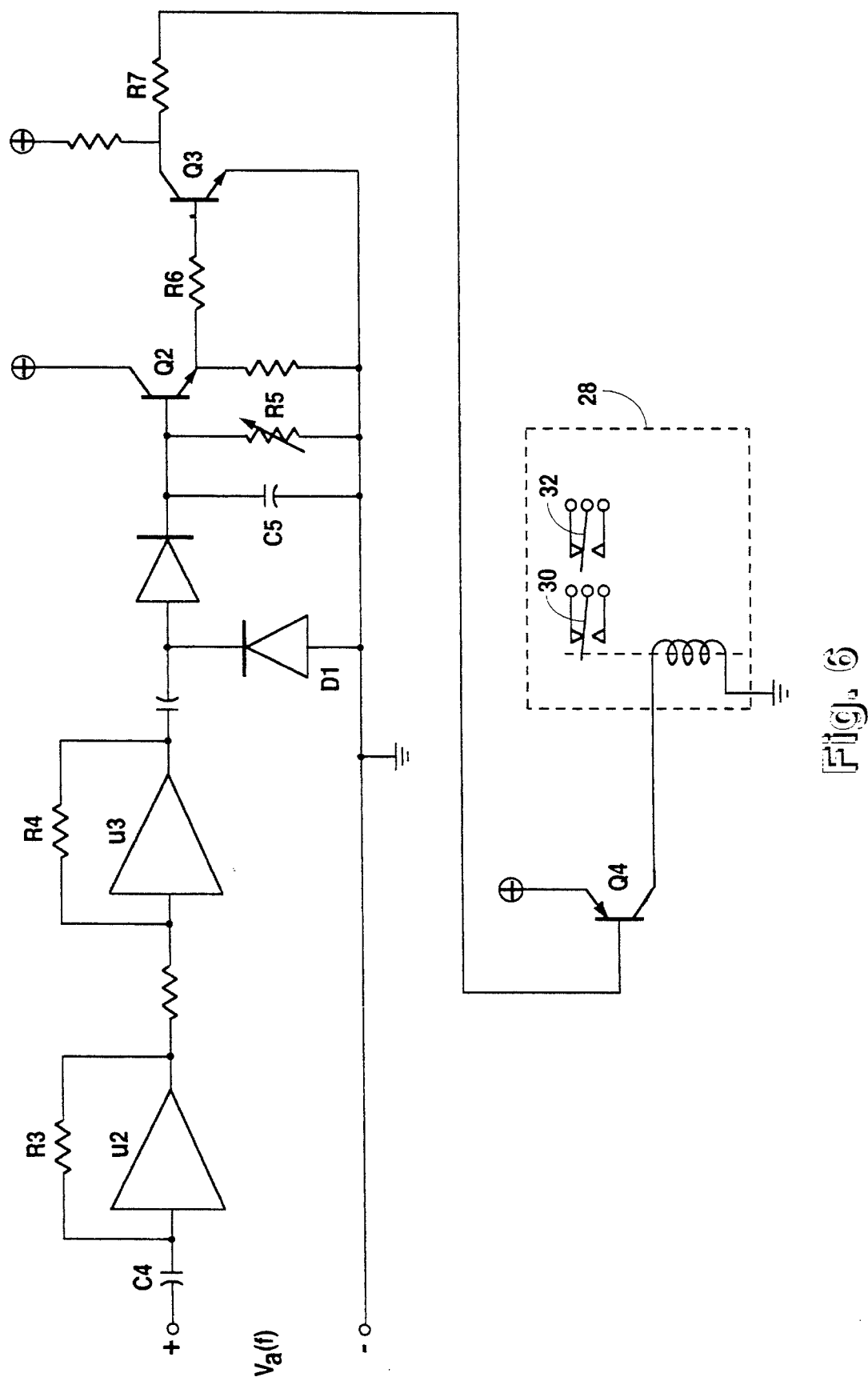
FIG. 6 is a circuit schematic of a voice-activated controller and associated switch for automatically selecting the input to the headset.

FIG. 6 shows a circuit schematic for a voice-activated controller circuit and associated relay switch. The audio output signal of the vehicular intercom system, $V_a(f)$, is tapped and supplied through coupling capacitor C4 to operational amplifiers U2 and U3 in series. Amplifiers U2 and U3 are preferably LM358 operational amplifiers, available from Texas Instruments. Resistors R3 and R4 are selected to achieve most of the gain in amplifier U2, with amplifier U3 functioning simply as a follower to isolate the audio signal. Diode D1 provides half-wave rectification of the output of amplifier U3. Variable resistor R5 allows the attack rate of VOX 34 to be set by the user, the attack rate being inversely proportional to the product of capacitor C5 and variable resistor R5. Transistor Q2 functions as a follower to provide further isolation of the amplified signal to prevent spurious activation of relay switch 28. Transistor Q3 provides further gain necessary to switch transistor Q4, the gain being proportional to the ratio of resistor R6 to resistor R7. The output of transistor Q3 drives transistor Q4, which in turn activates relay switch 28. Switch arms 30 and 32 of relay switch 28 are configured so that the presence of $V_a(f)$ at the input of VOX 34 causes $V_a(f)$ to be supplied to the input of the headset.

Although a currently preferred embodiment of the electronic stethoscope system has been described, changes or modifications will now occur to those skilled in the art without departing from the spirit or scope of the invention as set forth in the following claims.

I claim:

1. A stethoscopic system for use in high-noise environments, comprising:

transducer means for converting body sounds into an electrical output signal;

driver means for converting the electrical output signal of the transducer means into an acoustical pressure signal;

a summing microphone;

an active noise reduction circuit having an input signal received from the transducer means, an output signal transmitted to the driver means, signal received from the summing microphone;

a headset having an input signal, said headset providing an enclosure for the driver means and the summing microphone and forming a close-fitting acoustical seal with a listener's head at points on the listener's skull surrounding the ear so as to substantially attenuate acoustical noise originating external to the headset;

switch means for selecting either the electrical output signal from the transducer means or a voice signal from a vehicular intercom system as the input signal to the headset;

means for causing the switch means to select said voice signal as the input signal to the headset when said voice signal is present; and an amplifier electrically coupled between the transducer means and the switch means, said amplifier having a positive gain of at least 2000 substantially throughout the audio frequency range of cardiac and pulmonary auscultory sounds.

2. A stethoscopic system for use in high-noise environments, comprising:

transducer means for converting body sounds into an electrical output signal;

driver means for converting the electrical output signal of the transducer means into an acoustical pressure signal;

a summing microphone;

an active noise reduction circuit having an input signal received from the transducer means, an output signal transmitted to the driver means, and a feedback signal received from the summing microphone;

means for mounting the driver means and the summing microphone near a listener's ear;

switch means for selecting either the electrical output signal from the transducer means or a voice signal from a vehicular intercom system as the input signal to the active noise reduction circuit;

means for causing the switch means to select said voice signal as the input signal to the active noise reduction circuit when said voice signal is present; and an amplifier electrically coupled between the transducer means and the switch means, said amplifier having a positive gain of at least 2000 substantially throughout the audio frequency range of cardiac and pulmonary auscultory sounds.

3. A stethoscopic system for use in high-noise environments, comprising:

transducer means for converting body sounds into an electrical output signal;

driver means for converting the electrical output signal of the transducer means into an acoustical pressure signal;

a summing microphone for converting the ambient noise into an electrical error signal;

means for inversely feeding back the electrical error signal from the summing microphone to said driver means so as to substantially cancel the unwanted acoustical signal originating outside the headset;

a headset having an input signal, said headset providing an enclosure for the driver means and the summing microphone and forming an acoustical seal around a listener's ear so as to substantially attenuate acoustical noise originating external to the headset;

means for automatically switching the input signal to the headset from the electrical output signal of the transducer means to a voice signal of a vehicular intercom system when said voice signal is present; and an amplifier electrically coupled between the transducer means and the automatic switching means, said amplifier having a positive gain of at least 2000 substantially throughout the audio frequency range of cardiac and pulmonary auscultory sounds.

\* \* \* \* \*